United States Patent
Zhou et al.

(10) Patent No.: US 10,562,281 B2
(45) Date of Patent: Feb. 18, 2020

(54) COOLING SIGNAL DEVICE FOR USE IN AN ABSORBENT ARTICLE

(75) Inventors: Peiguang Zhou, Appleton, WI (US); Jun Zhang, Appleton, WI (US); Andrew Mark Long, Appleton, WI (US); Kaiyuan Yang, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1712 days.

(21) Appl. No.: 13/195,986

(22) Filed: Aug. 2, 2011

(65) Prior Publication Data
US 2013/0034719 A1 Feb. 7, 2013

(51) Int. Cl.
| | | |
|---|---|---|
| *B32B 27/08* | (2006.01) | |
| *B32B 27/18* | (2006.01) | |
| *A61F 13/42* | (2006.01) | |
| *B29C 48/08* | (2019.01) | |
| *B29C 48/21* | (2019.01) | |

(52) U.S. Cl.
CPC .............. *B32B 27/08* (2013.01); *A61F 13/42* (2013.01); *B32B 27/18* (2013.01); *A61F 2013/421* (2013.01); *B29C 48/08* (2019.02); *B29C 48/21* (2019.02); *B32B 2307/726* (2013.01); *B32B 2307/732* (2013.01); *B32B 2555/02* (2013.01); *Y10T 428/249953* (2015.04); *Y10T 428/31504* (2015.04); *Y10T 428/31786* (2015.04); *Y10T 428/31855* (2015.04)

(58) Field of Classification Search
None
See application file for complete search history.

(56) References Cited

U.S. PATENT DOCUMENTS

| | | | | |
|---|---|---|---|---|
| 3,815,602 | A * | 6/1974 | Johns et al. | 604/366 |
| 3,930,086 | A * | 12/1975 | Harmon | 428/131 |
| 3,971,379 | A * | 7/1976 | Chatterjee | 604/368 |
| 5,342,685 | A * | 8/1994 | Gobran | 428/355 BL |
| 6,051,317 | A * | 4/2000 | Brueggemann et al. | 428/378 |
| 6,140,551 | A * | 10/2000 | Niemeyer et al. | 604/367 |
| 6,375,963 | B1 | 4/2002 | Repka et al. | |

(Continued)

FOREIGN PATENT DOCUMENTS

| | | |
|---|---|---|
| DE | 102009016375 A1 | 10/2010 |
| JP | 2009247644 A * | 10/2009 |

(Continued)

OTHER PUBLICATIONS

Machine translation of JP 2009247644 A, retrieved May 29, 2014.*

(Continued)

*Primary Examiner* — Callie E Shosho
*Assistant Examiner* — Krupa Shukla
(74) *Attorney, Agent, or Firm* — Kimberly-Clark Worldwide, Inc.

(57) ABSTRACT

A signal device includes a signal composite made with a coextruded film having at least two layers, a polymer skin layer and a stimulation layer. The stimulation layer includes a cooling agent and a polymer binder. The stimulation layer may be about 50 to 98 percent by weight of the signal composite. The signal device may be used in an absorbent article to provide a cooling sensation after a body-fluid insult has taken place.

14 Claims, 15 Drawing Sheets

(56) References Cited

U.S. PATENT DOCUMENTS

| | | | |
|---|---|---|---|
| 8,853,487 B2* | 10/2014 | Takeuchi | A61F 13/42 604/361 |
| 2001/0006677 A1 | 7/2001 | McGinity et al. | |
| 2002/0169427 A1 | 11/2002 | Roe et al. | |
| 2003/0107149 A1 | 6/2003 | Yang et al. | |
| 2006/0089067 A1* | 4/2006 | Baker et al. | 442/62 |
| 2006/0247588 A1* | 11/2006 | Olson et al. | 604/361 |
| 2008/0147153 A1* | 6/2008 | Quincy et al. | 607/114 |
| 2009/0179069 A1 | 7/2009 | Schmidt et al. | |
| 2009/0297585 A1 | 12/2009 | Meyers et al. | |
| 2010/0152689 A1* | 6/2010 | Long et al. | 604/361 |
| 2011/0152806 A1 | 6/2011 | Zhou et al. | |
| 2011/0152816 A1 | 6/2011 | Zhou et al. | |

FOREIGN PATENT DOCUMENTS

| | | |
|---|---|---|
| WO | 2006042364 A1 | 4/2006 |
| WO | WO 2008/056001 | 5/2008 |
| WO | WO 2009/052421 | 4/2009 |

OTHER PUBLICATIONS

Partial professional translation of JP 2009247644 A, retrieved May 29, 2014.*
Mark Elliott, "Superabsorbent Polymers", BASF (http://chimianet.zefat.ac.il/download/Super-absorbant_polymers.pdf), retrieved May 31, 2014.*
Rajoo, Fabrex, retrieved Oct. 18, 2014.*
Professional translation of JP 2009247644 A, retrieved Jun. 2014.*
Definition of film from The FreeDictionary.com, retrieved Oct. 20, 2014.*

* cited by examiner

1. MATERIAL A
2. MATERIAL B
3. MATERIAL C
4. MATERIAL B'
5. MATERIAL C'
6. MATERIAL A'

A, A' = POLYMER SKIN LAYERS
B, B', C, C' = ACTIVE CHEMISTRIES OR FUNCTIONAL MATERIALS

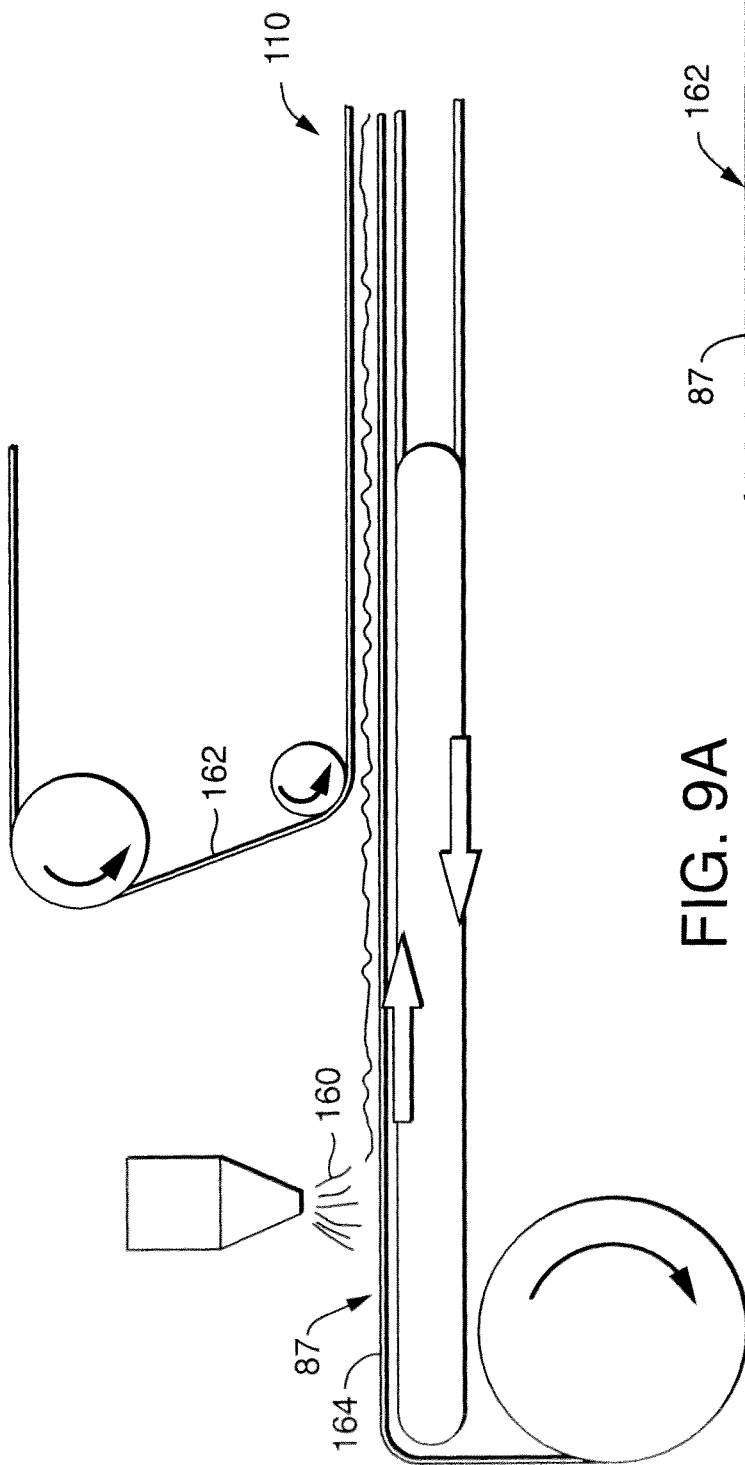
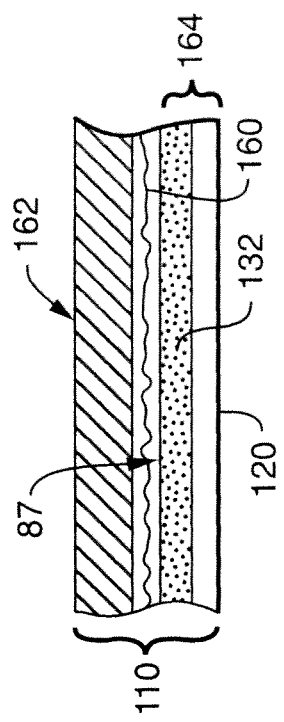
FIG. 9A
FIG. 9B

COOLING SIGNAL DEVICE FOR USE IN AN ABSORBENT ARTICLE

The present disclosure relates to cooling signal devices and a method of manufacture. More specifically, the disclosure relates to cooling signal devices that may be used in absorbent articles such as training pants, wherein the signal devices provide the wearer with a noticeable cooling sensation upon fluid insult.

BACKGROUND

Absorbent articles, such as children's training pants, for example, have been designed with temperature-change particles to provide a cooling sensation upon urination in an attempt to enhance a child's recognition of when urination occurs. As can be appreciated, such recognition can be an important step in the toilet training process. The temperature change sensation can often be the result of the stimulation material being positioned between the topsheet and the absorbent core of the article.

Unfortunately, in certain circumstances, the design of such articles may not be completely satisfactory. For example, the stimulation material included within the article can, in certain instances, be abrasive to the wearer. This abrasiveness can be particularly notable where the stimulation material is positioned close to the wearer's skin in use, which is generally a desirable configuration to maximize the temperature change sensation experienced by the wearer. In addition, the stimulation material either is or can become loose, thus resulting in shake-out or movement of the material. Moreover, the stimulation material may provide a rapid temperature change sensation, but it may not last as long as desired to assist with the toilet training process.

Previous attempts to create signal devices for providing a cooling sensation to a wearer include adding the active (a particulate) to the film either by 1) loading the particulate into the film directly, and 2) semi-entrapping the active on the surface of the film using a thermal compress roll. However, each of these methods produce a device that can only hold up to 50% active by weight due to negative effects on the film physical properties and characteristics such as strength, softness and loading ability. It is desirable to have a greater cooling sensation by being able to add more active materials to the signal device.

Thus, it is desirable to have a disposable absorbent article with a signal device that 1) can hold more than 50% active material, 2) can accommodate more than one active material, 3) is controllable in that it can delay or prolong the effects of the stimulation material, 4) secures the stimulation material to reduce or prevent movement of the material 5) has improved film strength properties, 6) prevents skin irritation, and/or 7) has a predetermined product shelf-life.

SUMMARY

In response to the needs discussed above, one aspect of an absorbent article with a signal device is presented. The signal device includes a signal composite that is made with a coextruded film having at least two layers, a first polymer skin layer and a stimulation layer. The stimulation layer includes a first cooling agent and a polymer binder. The stimulation layer is about 50 to 98 percent by weight of the signal composite.

In another aspect of the disclosure is a laminate signal composite including a coextruded film having two layers, an outer skin layer made with a water-soluble polymer, and a stimulation layer made with a cooling agent and a polymer binder. The stimulation layer is about 50 to 98 percent by weight of the coextruded film. The laminate includes another sheet of coextruded film having two layers, a second outer skin layer having a water-soluble polymer and a second stimulation layer made with a second polymer binder. The first coextruded film is bonded to the second coextruded film.

In yet another aspect of the disclosure is a method for making a signal composite including the steps of: coextruding a polymer skin layer and a first stimulation layer to form a film, wherein the first stimulation layer comprises a binder and a cooling agent, and wherein the cooling agent comprises 50 to 98 percent of the total weight of the signal composite, and wherein the polymer skin layer is 2 to 10 percent of the total weight of the signal composite.

The cooling signal devices may demonstrate one or more features with respect to storage and use of a product employing the cooling signal devices. For instance, skin irritation is greatly if not completely diminished due to the containment of any cooling agents within the structure of the signal device. Also, by containing the cooling agent in the signal device with a skin layer, premature activation due to humidity or sweating is prevented, either in storage or during use. Further, because the cooling agent is captured, dilution of the cooling agents is prevented. If the cooling agent were allowed to move about in an absorbent article employing the signal device, the cooling effect would be less concentrated and not as long lasting. Overall, when a cooling agent is loose within an absorbent article, it may be less effective than when the cooling agent is maintained in one section of the cooling signal device.

Numerous other features and advantages of the present disclosure will appear from the following description. In the description, reference is made to exemplary aspects of the disclosure. Such aspects do not represent the full scope of the disclosure. In the interest of brevity and conciseness, any ranges of values set forth in this specification contemplate all values within the range and are to be construed as support for claims reciting any sub-ranges having endpoints which are real number values within the specified range in question.

FIGURES

The foregoing and other features, aspects and advantages of the present disclosure will become better understood with regard to the following description, appended claims and accompanying drawings.

FIG. 1 representatively illustrates a front perspective view of a training pant with a mechanical fastening system of the pants shown fastened on one side of the training pant and unfastened on the other side of the training pant.

FIG. 2 representatively illustrates a plan view of the training pant of FIG. 1 in an unfastened, stretched and laid flat condition, showing the surface of the training pant that faces toward the wearer and having one aspect of a signal composite of the present disclosure.

FIG. 9a illustrates further exemplary process for constructing one aspect of a laminated signal composite of the present disclosure.

FIG. 9B illustrates one aspect of a signal composite made according to the exemplary process of FIG. 9A.

Figure 1:
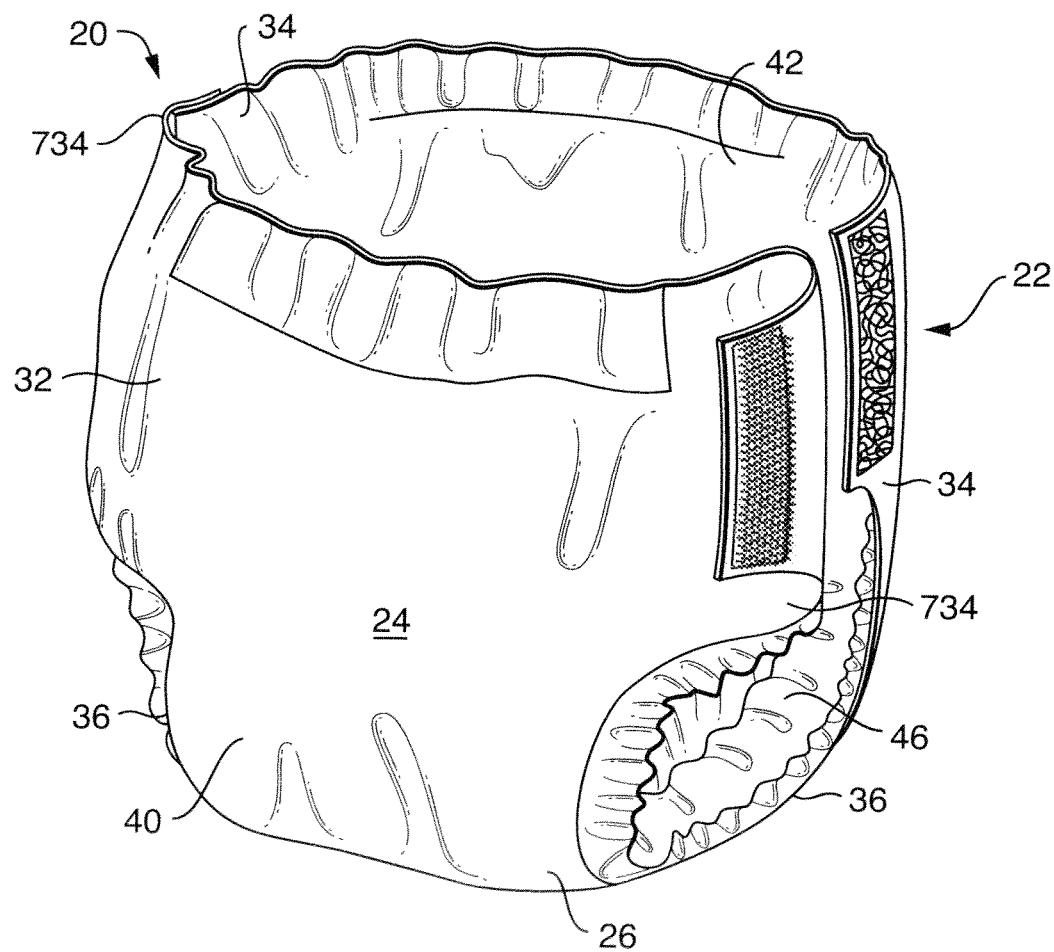

Repeated use of reference characters in the present specification and drawings is intended to represent the same or analogous features or elements of the present disclosure. The drawings are representational and are not necessarily drawn to scale. Certain proportions thereof may be exaggerated, while others may be minimized.

Definitions

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent GB 2,151,272 to Minto et al., each of which is incorporated herein by reference in a manner that is consistent herewith. The term "disposable" is used herein to describe absorbent articles that are not intended to be laundered or otherwise restored or reused as an absorbent article after a single use.

The terms "disposed on," "disposed along," "disposed with," or "disposed toward" and variations thereof are intended to mean that one element can be integral with another element, or that one element can be a separate structure bonded to or placed with or placed near another element.

The terms "elastic," "elasticized," "elasticity," and "elastomeric" and derivatives thereof mean that property of a material or composite by virtue of which it tends to recover its original size and shape after removal of a force causing a deformation.

The term "extensible" refers to a material or composite which is capable of extension or deformation without breaking, but does not substantially recover its original size and shape after removal of a force causing the extension or deformation (i.e., less than 40 percent recovery).

The term "fiber" refers to a continuous or discontinuous member having a high ratio of length to diameter or width. Thus, a fiber may be a filament, a thread, a strand, a yarn, or any other member or combination of these members.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, materials having contact angles less than 90 degrees are designated "wettable" or hydrophilic, and fibers having contact angles greater than 90 degrees are designated "non-wettable" or "hydrophobic".

The term "laminate" refers to a material where a film structure is adhesively or non-adhesively bonded to a web such as a nonwoven or tissue material.

The term "liquid impermeable," when used in describing a layer or multi-layer laminate, means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other optional materials are carried by the high velocity gas stream and are deposited on a collecting surface. The distribution and orientation of the meltblown fibers within the formed web is dependent on the geometry and process conditions. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241 to Butin et al. and U.S. Pat. No. 5,350,624 to Georger et al., each of which is incorporated herein by reference in a manner that is consistent herewith.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblown processes, spunbond processes, air laying processes, wet layering processes and bonded-carded-web processes.

The term "personal care absorbent articles" or "absorbent articles" in the context of this disclosure includes, but is not limited to diapers, diaper pants, training pants, absorbent underpants, incontinence products, and urinary shields; and the like.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "% by weight," "weight %," "wt %" or derivative thereof, when used herein, is to be interpreted as based on the dry weight, unless otherwise specified. These terms may be defined with additional language in the remaining portions of the specification.

DETAILED DESCRIPTION

The present disclosure describes a signal device. Such device comprises a signal composite formed into a sheet made by an extrusion process, and possibly, an additional lamination step. The signal composite includes at least one "skin" layer and at least one layer of a cooling agent/binder blend. The signal composite can includes about 50-98 percent cooling agent. This is in contrast to other prior signal composites that can only accommodate 50 percent or less of the cooling agent.

As described herein, the skin layer may be a water soluble polymer that serves to prevent premature activation of the cooling agent, or a water swellable polymer that allows water-based liquids to pass through to the cooling agent, or a combination thereof. The cooling agent, held together by a water soluble binder, is activated by the liquid resulting in a temperature drop or perceived temperature drop of the signal composite. The signal composite, the method of making the signal composite with or without an additional lamination step and an exemplary absorbent article utilizing the signal composite are further described herein.

Exemplary Absorbent Article

The signal device is useful in disposable absorbent articles. An absorbent article of the present disclosure generally can have an absorbent core, and can optionally include a topsheet and/or a backsheet, where the absorbent core can be disposed between the topsheet and the backsheet. To gain a better understanding of the present disclosure, attention is directed to FIGS. 1 and 2 for exemplary purposes showing a training pant and a signal composite of the present disclosure.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

Figure 2:
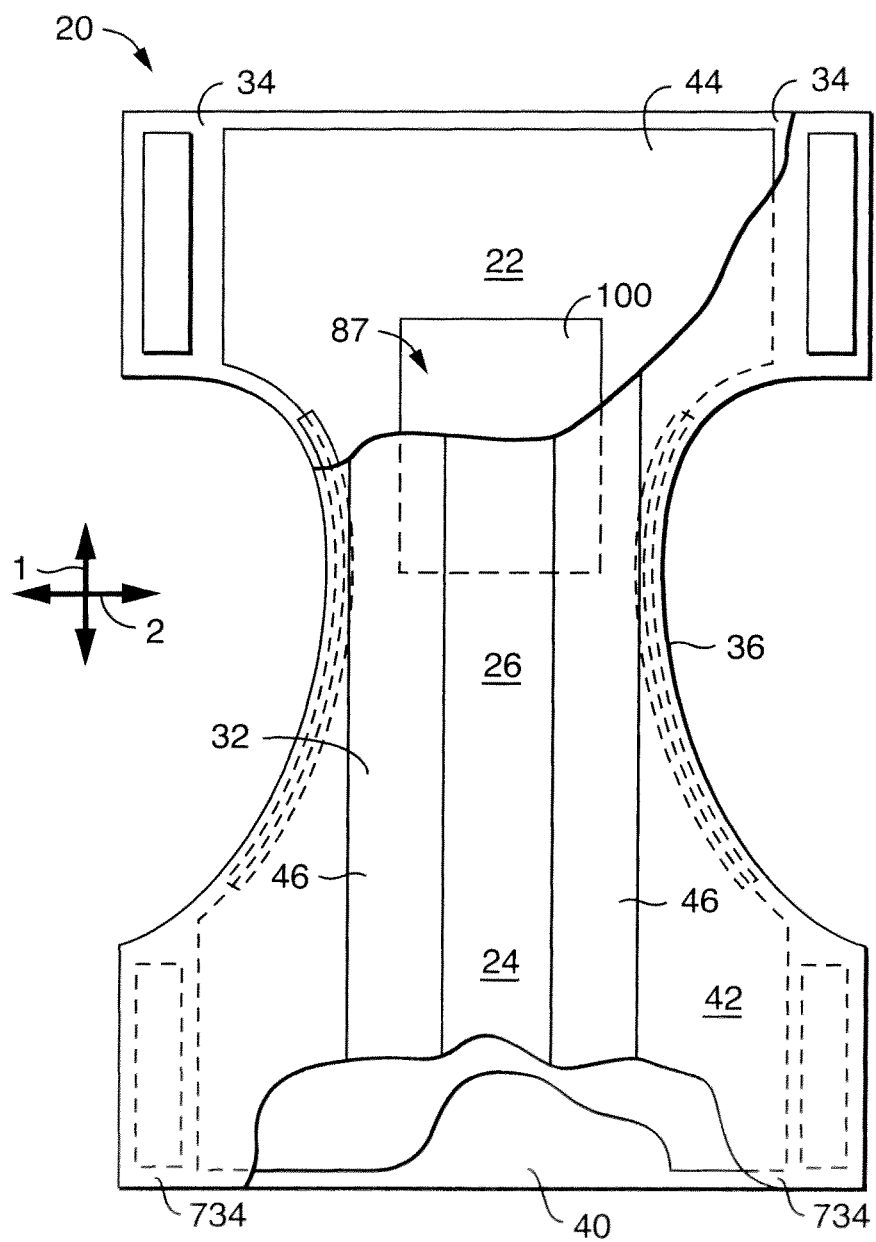

FIG. 1 illustrates a training pant 20 in a partially fastened condition, and FIG. 2 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions. The pant 20 also defines an inner surface (i.e., body-facing surface) adapted in use (e.g., positioned relative to the other components of the pant) to be disposed toward the wearer, and an outer surface (i.e., garment-facing surface) opposite the inner surface. The training pant 20 has a pair of laterally opposite side edges 36 and a pair of longitudinally opposite waist edges.

The illustrated pant 20 may include a chassis 32, a pair of laterally opposite front side panels 34 extending laterally outward at the front region 22 and a pair of laterally opposite back side panels 734 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. The backsheet 40 may be constructed of a nonwoven material. The backsheet 40, may be a single layer of a fluid impermeable material, or alternatively may be a multi-layered laminate structure in which at least one of the layers is fluid impermeable.

Examples of suitable backsheet 40 materials are spunbond-meltblown fabrics, spunbond-meltblown-spunbond fabrics, spunbond fabrics, or laminates of such fabrics with films, or other nonwoven webs; elastomeric materials that may include cast or blown films, meltblown fabrics or spunbond fabrics composed of polyethylene, polypropylene, or polyolefin elastomers, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. Examples of suitable surge management layers are described in U.S. Pat. No. 5,486,166 to Bishop et al.; U.S. Pat. No. 5,490,846 to Ellis et al.; and U.S. Pat. No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, 1-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core 44 can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core includes cellulose fiber and/or synthetic fiber, such as meltblown fiber, for example. Thus, in some aspects, a meltblown process can be utilized, such as to form the absorbent core 44 in a coform line. In some aspects, the absorbent core 44 can have a significant amount of stretchability.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present disclosure in the absorbent core 44 can be at least about 5% by weight of the core, such as at least about 30%, or at least about 50% by weight of the core, or between about 5% and 90%, such as between about 10% and 70% or between 10% and 50% by weight of the core. In still other aspects, the absorbent core 44 can optionally comprise about 35% or less by weight unmodified fluff, such as about 20% or less, or 10% or less by weight unmodified fluff.

It should be understood that the absorbent core 44 is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include a foam.

Signal Device

Figure 6:
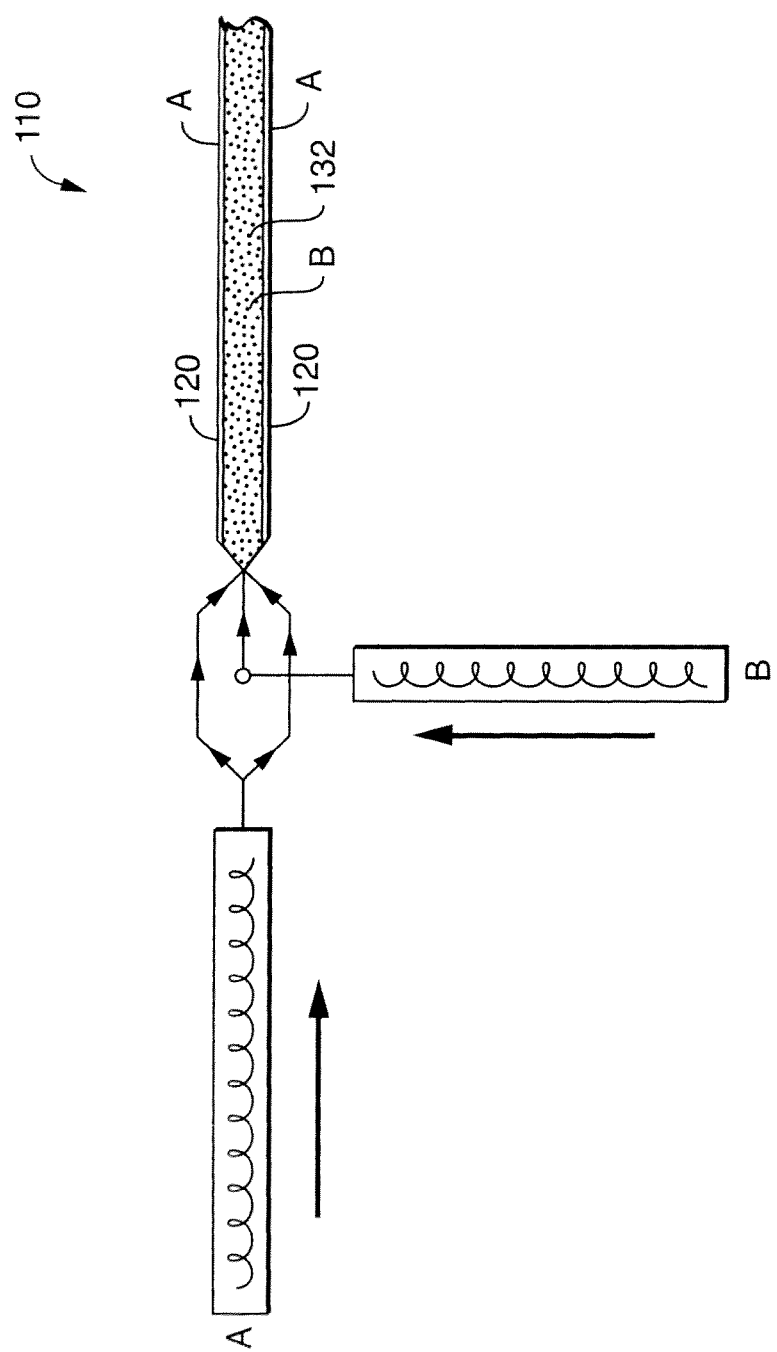
FIG. 6 shows a schematic of another exemplary process for constructing the signal composite of the present disclosure as seen in FIG. 3B.

Referring to FIG. 2, the disposable absorbent article 20 of the present disclosure includes a signal device 100 made using a signal composite 100 (see FIG. 6 for one non-limiting example of a signal composite 110). The signal device 100 is positioned in the absorbent article 20 to create a distinct physical sensation as the article 20 is insulted with an aqueous liquid. The signal device 100 has a longitudinal-direction 1 and a transverse-direction 2, which together form a plane when in a laid-flat condition, hereinafter referred to as the "x-y plane." The signal composite 110 from which the signal device is made has a z-direction (not shown) that is perpendicular to the x-y plane, and which corresponds to the thickness of the signal composite 110. The signal device 100 includes a body-facing surface 87 intended to be disposed toward the wearer in use (i.e., an inner surface); and an opposite garment-facing surface (not shown) intended to be disposed away from the wearer in use (i.e., an outer surface).

The signal device 100 as illustrated in the figures is generally rectangular. However, the signal device 100 can have any desired shape. For example, it may be rectangular shaped, triangular shaped, circular-shaped, oval shaped, race-track shaped, I-shaped, generally hourglass shaped, T-shaped and the like. In some aspects, the signal device 100 may have a random shape. Thus, the dimensions in at least the x-y plane can vary as desired.

Because the physical sensation resulting from the signal composite 110 is noticeable to the wearer, the wearer's ability to recognize when a liquid insult has occurred (and/or is occurring) will be enhanced. The signal device 100 may be positioned within the article 20 in any operative location such that a user may detect a physical sensation as a result of the signal composite 110 receiving an aqueous liquid insult. For example, the signal device 100 may be disposed adjacent to and in contact with the body-facing surface 87 of an absorbent core 44. In the alternative, the signal device 100 may be disposed adjacent to and in contact with the garment-facing surface and/or the body-facing surface 87 of a topsheet 42. In still another alternative, the signal device 100 may be disposed adjacent to and in contact with the body-facing surface 87 or garment-facing surface of a surge layer, for example. Other configurations are also suitable for the disclosure as would be readily apparent to those skilled in the art.

In some aspects, the signal device 100 may be attached in an absorbent article, such as to the absorbent core, a surge layer and/or a topsheet for example, by bonding means known in the art, such as ultrasonic, pressure, adhesive, aperturing, heat, sewing thread or strand, autogenous or self-adhering, or the like, and combinations thereof. In other aspects, the signal composite 110 may be free-floating within the article. In addition, the signal device 100, made from the signal composite 110, may be present in the article 20 as a single layer or as multiple layers, such as strips arranged in a side-by-side configuration.

Signal Composite

Figure 3A:
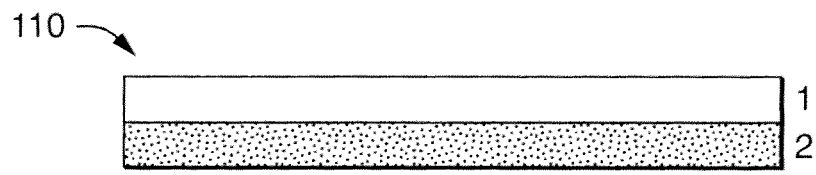
FIGS. 3 (A-E) are side views of several non-limiting aspects of a signal composite of the present disclosure.
Figure 3B:
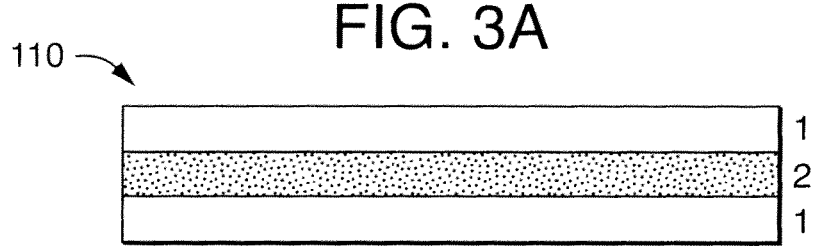
Figure 4:
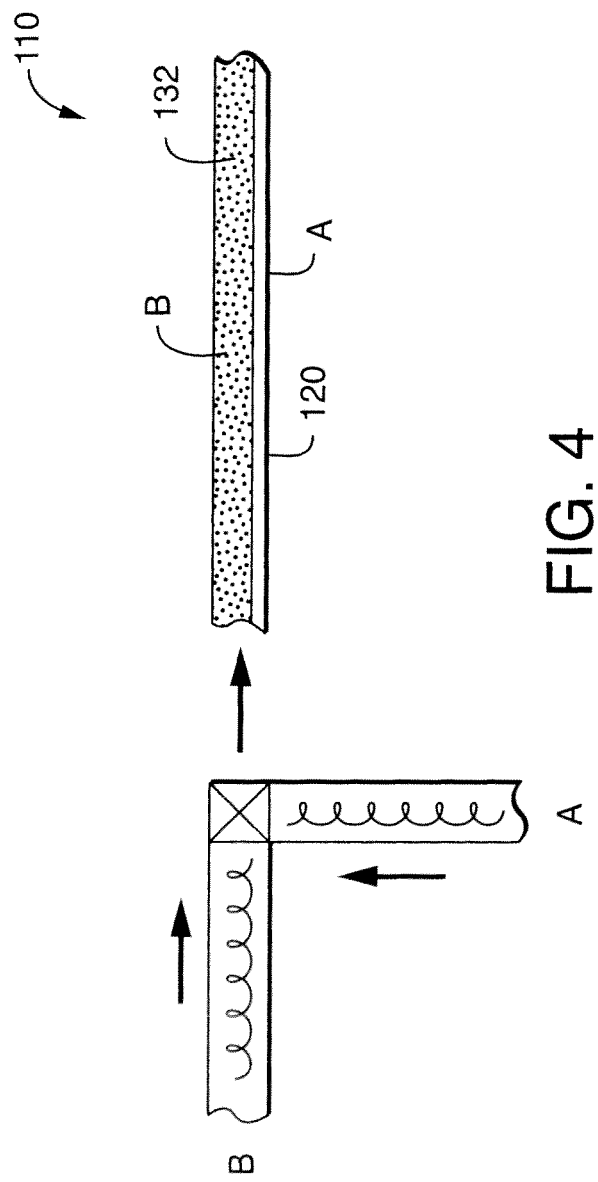
FIG. 4 shows a schematic of one exemplary process for constructing the signal composite of the present disclosure as seen in FIG. 3A.

Referring now to FIG. 4, in one aspect, the signal composite 110 of the present disclosure is an extruded film having at least two layers, a skin layer 120 and a stimulation layer 132. The skin layer 120 may be water swellable or water soluble either completely or in varying degrees. The water-soluble and/or water-swellable polymer can be modified thermal starch, polyvinyl alcohol, acrylic polymer, polyethylene oxide, polyethylene glycol, polyacrylamide, polyester, ethylene vinyl acetate copolymer, any other suitable material, and combinations thereof. The stimulation layer 132 contains a cooling agent 134 held together with a binder 136 (see example stimulation layer shown in FIG. 15). In some aspects, the stimulation layer 132 is sandwiched between two skin layers 120 such as that shown in FIG. 3B.

The signal composite 110 may have a desired stiffness or flexibility. In some desirable aspects, the signal composite 110 may have approximately the same or more flexibility as the overall flexibility of the absorbent core 44.

As mentioned, the signal composite 110 has a thickness dimension in the z-direction. By way of example only, a suitable thickness of the signal composite 110 may be between 0.2 mm and 10 mm, such as between 0.25 mm and 5 mm or between 0.5 mm and 3 mm as measured by the Thickness Test.

Figure 3C:
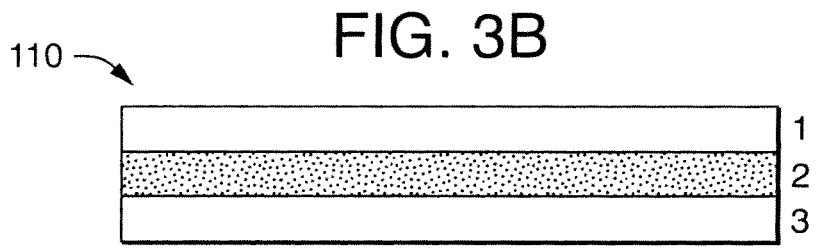
Figure 3D:
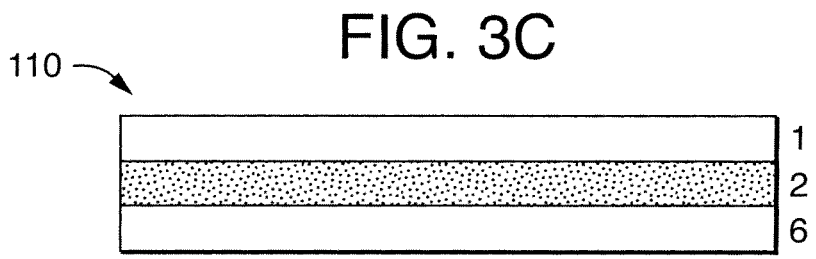
Figure 3E:
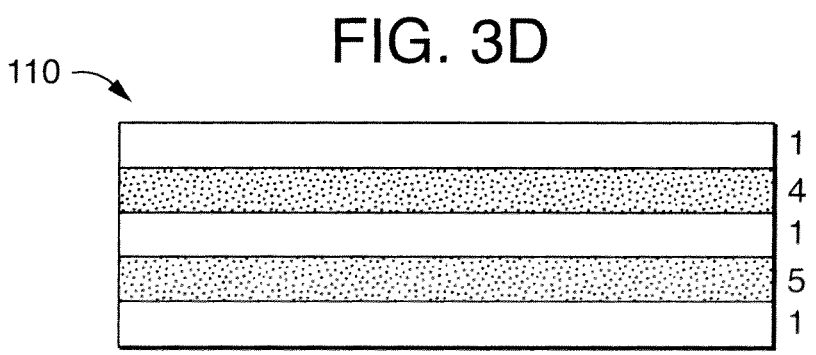

The thickness of the signal composite 110 skin layer as seen in FIGS. 3 (A-D) may be from about 0.001 mm to about 0.10 mm, such as 0.01 mm to 0.10 mm, or 0.025 mm to 0.075 mm If there is more than two skin layers 120 and one stimulation layer 132 such at the signal composite 110 as seen in FIG. 3E, then the thickness of the signal composite 110 skin layer may be from about 0.001 mm to about 0.10 mm, such as 0.02 mm to 0.08 mm, or 0.025 mm to 0.05 mm The skin layer thickness may be controlled, as well as its speed of dissolution or swelling. Thus, the time and intensity aspects of the cooling can be controlled.

The signal composite 110 as seen in FIGS. 3 A-D may suitably have a basis weight of about 10 gsm to about 1000 gsm, such as about 100 gsm to about 800 gsm, or about 200 gsm to about 800 gsm. If there is more than two skin layers 120 and one stimulation layer 132 such at the signal composite 110 as seen in FIG. 3E, then the signal composite 110 may suitably have a basis weight of about 10 gsm to about 1000 gsm, such as about 50 gsm to about 800 gsm, or about 100 gsm to about 500 gsm.

Cooling Agents

Figure 15:
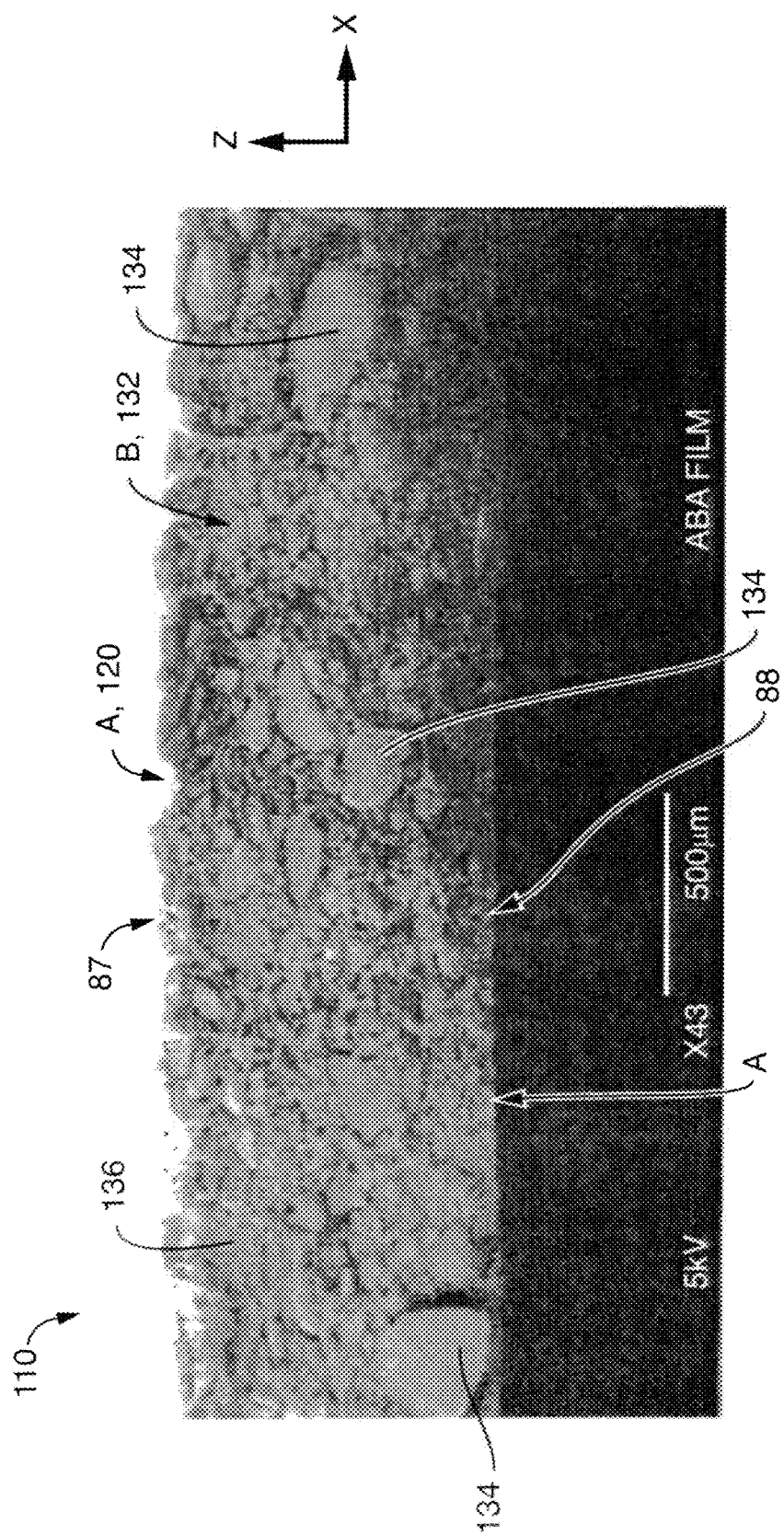
FIG. 15 is an SEM photograph of the aspect represented by FIG. 3B.

Referring to FIG. 15, each stimulation layer 132 includes a cooling agent 134. The purpose of the cooling agent 134 is to provide the user with a perceptible sensation when a fluid insult is occurring and/or has occurred. This sensation is the result of an actual temperature drop or a stimulating material that provides the perception of a temperature drop.

The cooling agent 134 is desirably in the form of a solid which may include particles, flakes, fibers, agglomerates, granules, powders, spheres, pulverized materials, or the like, as well as combinations thereof. The solids may have any desired shape such as, for example, cubic, rod-like, polyhedral, spherical or semi-spherical, rounded or semi-rounded, angular, irregular, and the like. Desirably, the cooling agent is provided in particulate form for ease of processing in the described aspects.

As can be appreciated, the signal composite 110 may define a total amount of cooling agent 134, by weight. For example, in some aspects, each stimulation layer 132 may include about 30 percent to about 98 percent cooling agent 134, such as about 50 percent to about 95 percent cooling agent 134, or about 75 percent to about 90 percent cooling agent 134. The signal composite 110 overall may include about 50 to about 95 percent stimulation material by weight.

Alternatively, the amount of cooling agent 134 can be expressed in terms of basis weight. Accordingly, the basis weight of each stimulation layer 132 may range from about 10 grams/m$^2$ (gsm) to about 100 gsm, such as about 100 gsm to about 800 gsm, or about 200 gsm to about 600 gsm.

The solubility of such cooling agents 134 when contacted with an aqueous liquid is desirably from about 0.01 to about 6 grams of material per gram of water (g/g), such as from about 0.1 g/g to about 3 g/g.

As mentioned, the cooling agent 134 is responsive to contact with an aqueous solution (such as urine or other aqueous body exudates) to provide a cooling effect. In one aspect, a mechanism by which this is accomplished is by dissolution of the cooling agent 134 in the aqueous solution. For example, the cooling agent 134 may include particles that have a substantial energy difference between a dissolved state and a crystalline state so that energy in the form of heat is absorbed. In the alternative, cooling agent 134 may include particles that provide the sensation of a substantial energy difference.

Reference is made to U.S. Patent Application Publication 2004/0254549 to Olson, et al., incorporated herein by reference in a manner that is consistent herewith, for additional information regarding the mechanism by which a sensation of temperature reduction is accomplished.

To illustrate, the signal composite 110 may suitably provide a temperature change when insulted with an aqueous liquid of at least about 2° C., such as at least about 5° C., or at least about 10° C., or between 3° C. and 15° C.

In one aspect, polyols such as xylitol particles may be selected as a cooling agent 134. A cooling sensation occurs because xylitol particles absorb heat when dissolved in an aqueous liquid. Alternatively, other polyols such as sorbitol or erythritol may be advantageously selected to provide a cooling sensation. In yet other aspects, various combinations of the above cooling agents 134 may be utilized. Suitable polyols can be obtained from Roquette America, Inc., a company having offices in Keokuk, Iowa, U.S.A., under the trade name of XYLISORB (xylitol) or NEOSORB (sorbitol). Such polyols can generally be obtained from the manufacturer in particular particle sizes, such as 90 microns, 300 microns, 500 microns, and the like for disposition in the stimulation layers 132.

Other suitable cooling agents 134 that absorb heat during dissolution include salt hydrates, such as sodium acetate ($H_2O$), sodium carbonate ($H_2O$), sodium sulfate ($H_2O$), sodium thiosulfate ($H_2O$), and sodium phosphate ($H_2O$); anhydrous salts such as ammonium nitrate, potassium nitrate, ammonium chloride, potassium chloride, and sodium nitrate; organic compounds such as urea and the like or combinations thereof.

In addition, as referenced above, in some aspects, the disposable absorbent article 20 desirably provides a surface temperature change when wet of from about 2° C. to 15° C. as determined by the Digital Thermal Imaging test described herein. To achieve this result, the temperature change substance and the amount used should be selected so that the possible total energy change is from about 1 to about 30 calories per square centimeter ($cal/cm^2$), which may represent either a possible total energy release of from about 1 to about 20 $cal/cm^2$ or a possible total energy absorption of from about 2 to about 15 $cal/cm^2$, or such as from about 3 to about 10 $cal/cm^2$.

Temperature change agents that absorb heat on contact with an aqueous solution desirably have a heat of solution, hydration, or reaction greater than about 5 cal/g, or less than about −120 cal/g. The heat of solution, hydration, or reaction is suitably within the range of from about 30 to about 90 cal/g or from about −30 to about −90 cal/g, such as from about 30 to about 70 cal/g or from about −30 to about −70 cal/g, such as xylitol at −32 cal/g or urea at −60 cal/g.

Binders

Examples of suitable binder materials include polyethylene oxide (PEO); polyethylene glycol (PEG); polyvinyl alcohol (PVOH); starch derivatives such as starch ethers, carboxymethyl starch, cationic starch, hydroxyalkyl starch, and the like, for example hydroxyethyl starch, hydroxypropyl starch and hydroxybutyl starch; cellulose derivatives such as cellulose ethers, hydroxyalkyl cellulose, for example hydroxyethyl cellulose, hydroxypropyl cellulose, methylcellulose, methyl propyl cellulose, carboxymethyl cellulose, and the like; polyacrylic acid, polyacrylamide; polyvinylmethyl ether; carrageenan; water-soluble alkyd resins; or the like, ethylene vinyl acetate copolymer (EVA) and combinations thereof. In addition, thermoplastic adhesive fibers, such as thermoplastic binder fibers, can also be used.

Signal Composite Manufacture

The signal composite 110 may be manufactured by an extrusion process either alone or in combination with a lamination process. It is contemplated that a signal composite 110 that is extruded to form a film may be laminated to other films, or webs of tissue or nonwoven materials.

It is understood that signal composite 110 is not limited to any number of stimulation layers 132. Rather, the signal composite 110 can have any number of stimulation layers 132 with the only limitation being the number of extruded layers that may be bonded to other layer(s) by lamination or coextrusion. Because the skin layers 120 are so thin with respect to the stimulation layers 132, the film may have any number of skin layers 120 as is practical.

Extrusion

Generally, a multifunctional film/sheet containing 90% active material in particle or powder form may be made through a co-extrusion process. FIG. 3 shows a small set of exemplary stimulation composite aspects 3A-D, manufactured using the extrusion methods described herein. (Components of aspects 3A-E are described by a legend located on the lower left sector of the drawing page.) The present disclosure is not limited to this very small set of examples. There are hundreds of layer combinations possible (for instance, a 5-layer signal composite has 120 possible combinations). Further, there is no significance as to which "layer" is located on top when one views the drawings in a top-to-bottom fashion.

In the example shown in FIG. 3A, there are two layers that form one a signal composite 110. Desirably, layer 1 is a polymer skin layer. Layer 2 may include an active chemistry such as the cooling agent described herein. Layer 2 also includes a binder material, also described herein. This is an example of an extruded AB structure.

In the example shown in FIG. 3B, there are three layers that together form one embodiment of the signal composite 110. Desirably, layers 1 are identical types of polymer skin layers. The middle layer, layer 2, includes an active chemistry such as the cooling agent described herein. The middle layer further includes a binder material as described herein. This is an example of an extruded ABA structure as seen in FIG. 15.

In the example shown in FIG. 3C, there are three layers that together form a signal composite 110. Desirably, layers 1 and 6 are different types of polymer skin layers. The middle layer, layer 2, includes an active chemistry such as the cooling agent described herein. The middle layer may also include a binder material, also described herein. This is an example of an extruded ABA' structure.

In the example shown in FIG. 3D, there are three layers that together form one embodiment of the signal composite 110. Desirably, layer 1 is one type of polymer skin layer. The middle layer, layer 2, includes an active chemistry such as the cooling agent described herein. The middle layer may also include a binder material, also described herein. The layer 6 may be another layer with active chemistry. This is an example of an extruded ABC structure.

In the example shown in FIG. 3E, there are five layers that together form a signal composite 110. Here, layers 1 are identical types of polymer skin layers. The middle layer 4 includes an active chemistry such as the cooling agent described herein. The middle layer 4 may also include a binder material, also described herein. Likewise, the middle layer 5 includes an active chemistry such as the cooling agent described herein. The middle layer 5 may also include a binder material, also described herein. This is an example of an extruded and laminated AB'AC'A structure.

Referring now to FIG. 4, shown is a schematic drawing of a simple two-layer extrusion process. Generally, the stimulation layer 132 (including binder 136 and cooling agent 134 as previously described) is coextruded with a skin layer 120 to create an extruded AB structure.

Figure 5:
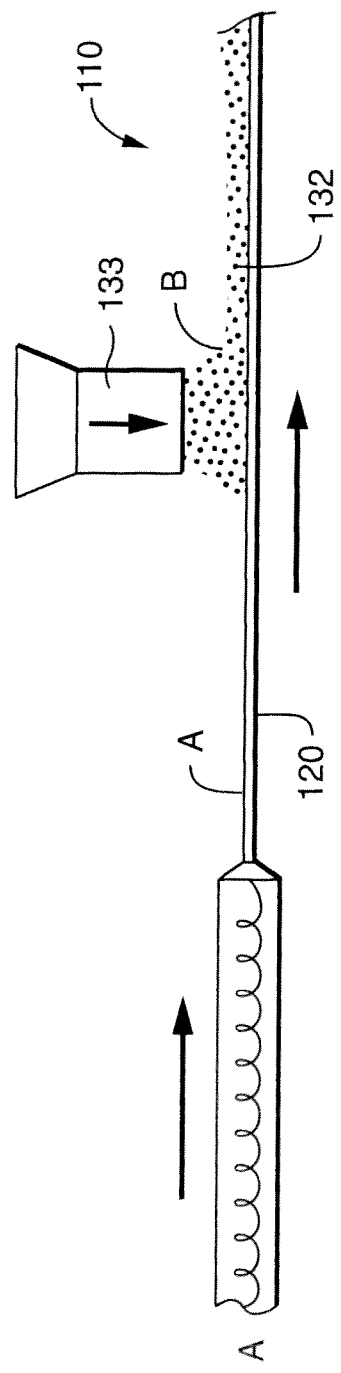
FIG. 5 shows a schematic of another exemplary process for constructing the signal composite of the present disclosure as seen in FIG. 3A.

Referring now to FIG. 5, shown is a schematic drawing of a simple one-layer extrusion process. Generally, the stimulation layer 132 (including binder 136 and cooling agent 134 as previously described) is applied from a particulate feeder 133 to the extruded skin layer 120 to create an AB structure.

Referring now to FIG. 6, shown is a schematic drawing of a three-layer extrusion process. Generally, the stimulation layer 132 is coextruded so that it is disposed between two skin layers 120 to create an extruded ABA structure.

Lamination

Lamination may be used to create signal composites 110 that have more film layers that can be made by the extrusion process, or to create signal composites 110 by attaching extruded films to materials that cannot be extruded.

Figure 7:
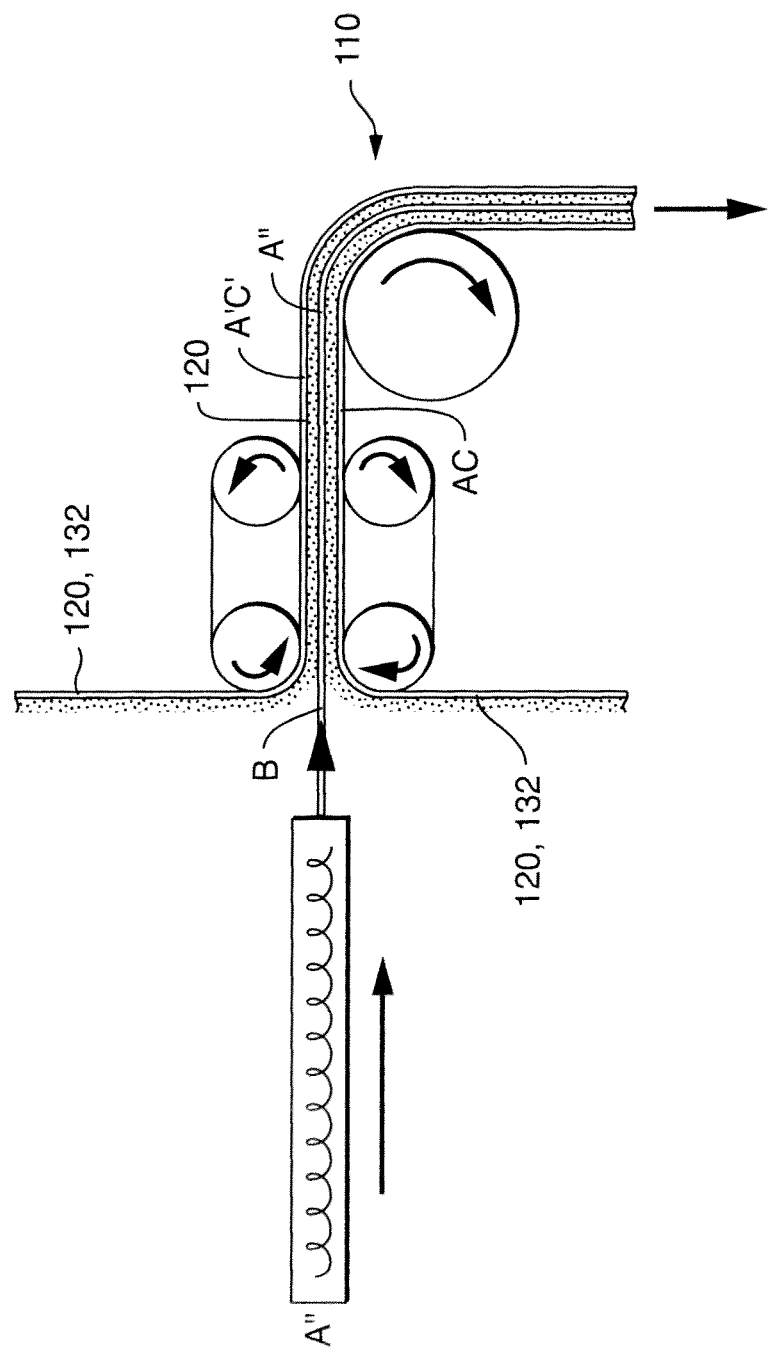
FIG. 7 shows a schematic of a further exemplary process for constructing a signal composite of the present disclosure.

Referring now to FIG. 7, shown is a schematic drawing of a lamination process wherein there are two extruded films AC and A' C' that are bonded directly together by an extruded skin layer A". The layers A and A' and A" are all skin layers 120. Layers C and C' are stimulation layers 132 made from binder 136 and cooling agent 134. The result of this lamination process is an ACA"C'A' structure.

Figure 8:
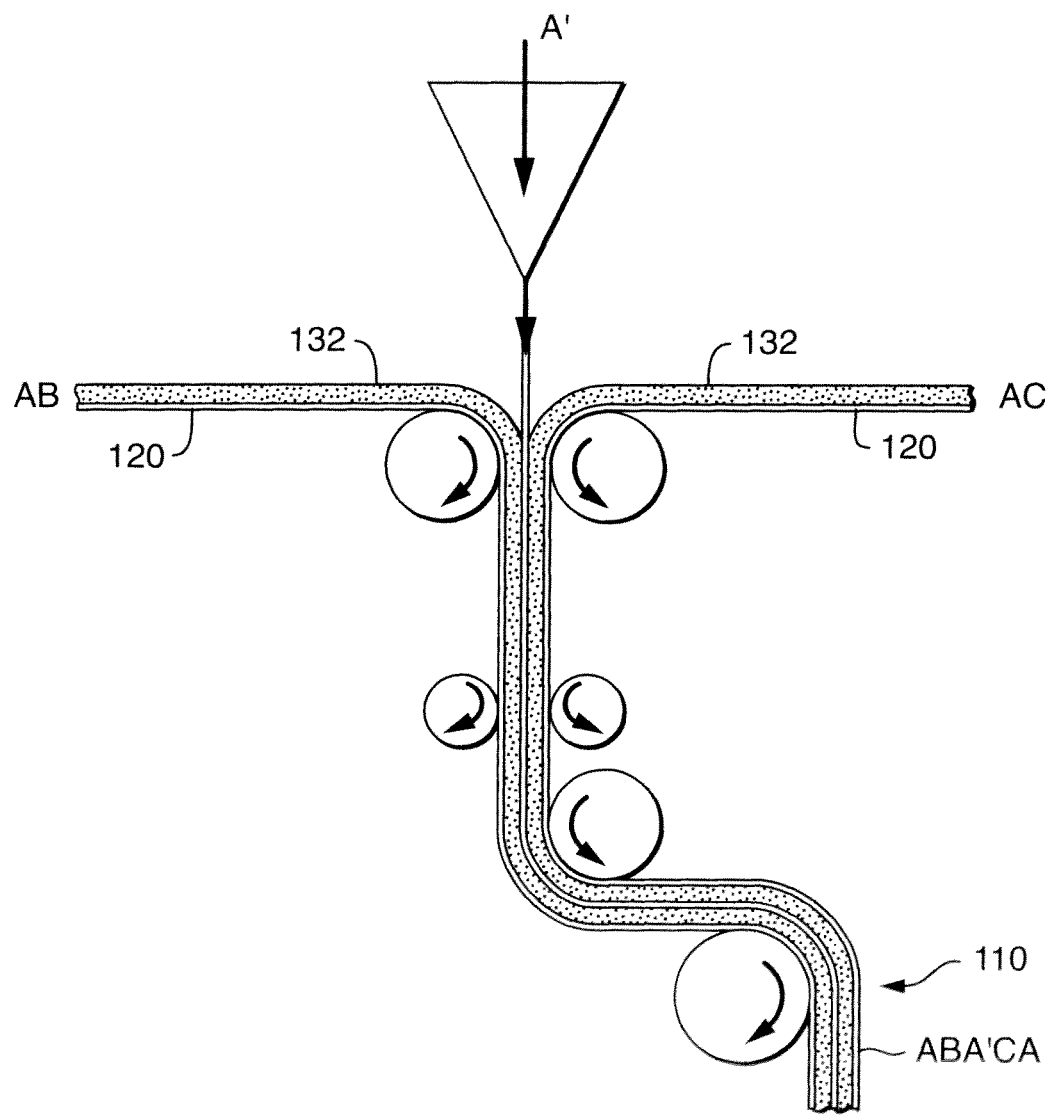
FIG. 8 shows a schematic of yet a further exemplary process for constructing a signal composite of the present disclosure.

Referring now to FIG. 8, two coextruded films are bonded together by way of lamination; one film having an AB construction, and another film having an AC construction. Each A component (skin layer 120), and the respective layers B and C (both stimulation layers 132) are directly bonded to one another with a hot-melt adhesive as described herein, and shown as layer A'. Through the process depicted, the structure ABA'CA is formed and defines a signal composite 110. Through further lamination, other layers may be combined to form the ABA'CA.

In another variation of FIG. 8 (not shown), the signal composite includes a first coextruded film having two layers AB, a first outer skin layer 120 having a water-soluble polymer, and a first stimulation layer 132 having a cooling agent and a first polymer binder. The first stimulation layer 132 comprises 50 to 90 percent by weight of the first coextruded film.

A second coextruded film may have two layers, a second outer skin layer 120 having a water-soluble polymer, and a second stimulation layer 132 having a second polymer binder; and an adhesive A' that attaches the first coextruded film to the second coextruded film to form signal composite 110.

Referring now to FIGS. 9A and 9B, it may be desirable to further attach, by way of lamination, a non-extrudable liquid pervious layer 162 to the body-facing surface 87 of an extruded film 164. The additional liquid-pervious layer 162 can be included for many reasons, including but not limited to providing a way to include a printed graphic on the signal composite 110, or numerous other desires. Liquid permeable materials suitable for the additional liquid pervious layer 162 include tissue layers; nonwovens such as meltblown, coform, spunbond, spunbond-meltblown-spunbond (SMS), bonded-carded-web (BCW), woven fabric, perforated films, foam layers, and the like. The additional liquid pervious layer 162 may suitably have a basis weight of about 10 gsm to about 50 gsm, such as about 10 gsm to about 30 gsm, or about 10 gsm to about 20 gsm. An adhesive layer 160 bonds the film 164 to the layer 162.

When a laminate is formed using these methods, a hot-melt adhesive may or may not be employed (if the laminas are in a molten state, no adhesive is needed). A hot-melt adhesive may contain from about 15 to about 50 weight percent cohesive strength polymer or polymers; from about 30 to about 65 weight percent resin or other tackifier or tackifiers; from more than zero to about 30 weight percent plasticizer or other viscosity modifier; and optionally less than about 1 weight percent stabilizer or other additive. Other hot-melt adhesive formulations comprising different weight percentages of these components are possible.

Examples of suitable materials include hydrophobic and hydrophilic hot melt polymers, such as those available from National Starch and Chemical Co. (having a place of business located in Bridgewater, N.J., U.S.A.) such as 34-5610, 34-447A, 70-3998 and 33-2058; those available from Bostik-Findley (having a place of business located in Milwaukee, Wis., U.S.A.) such as HX 4207-01, HX 2773-01, H2525A, H2800; and those available from H.B. Fuller Adhesives (having a place of business located in Saint Paul, Minn., U.S.A.) such as HL8151-XZP. Other adhesives are further described in U.S. Patent Publication No. 2005/0096623 to Sawyer, et al., which is incorporated herein by reference in a manner that is consistent herewith.

It is also contemplated that alternative adhesives may be used without departing from the scope of this disclosure. Examples of alternative adhesives include polyethylene oxide (PEO); polyethylene glycol (PEG); polyviny alcohol (PVOH); starch derivatives such as starch ethers, carboxymethyl starch, cationic starch, hydroxyalkyl starch, and the like, for example hydroxyethyl starch, hydroxypropyl starch and hydroxybutyl starch; cellulose derivatives such as cellulose ethers, hydroxyalkyl cellulose, for example hydroxyethyl cellulose, hydroxypropyl cellulose, methylcellulose, methyl propyl cellulose, carboxymethyl cellulose, and the like; polyacrylic acid; polyvinylmethyl ether; carrageenan; water-soluble alkyd resins; or the like, ethylene vinyl acetate copolymer (EVA) and combinations thereof. In addition, thermoplastic adhesive fibers, such as thermoplastic binder fibers, can also be used.

Permeability

In some aspects, it is desirable that the skin layers 120 and binder 136 are liquid permeable. However, in cases where the skin layers 120 and binder 136 are not inherently liquid permeable, the stimulation composite 110 may be made permeable by perforation. The resulting perforations may have a density of about 15 to about 20 percent of the surface area of the signal device 100, and may be up to about 2 mm in diameter or of an equivalent dimension should the perforations be a shape other than circular. Methods for perforating materials are well-known in the art, and include, but are not limited to, needle-punch, air-jet, and the like. In other aspects, it is desirable that the skin layer 120 and binder 136 are water-soluble.

In an alternative aspect, the signal composite 110 has a skin layer 120 that contains both a water soluble polymer and a water swellable polymer. Water molecules can make contact with the cooling agent by dissolving the water soluble polymer. Further, the water swellable polymer swells to prevent a solution of cooling agent and excess water molecules from freely moving out of the signal device 100. By preventing the solution from leaving the signal device 100, the cooling sensation lasts longer and prevents any possible skin irritation or other such concerns.

EXAMPLES

Various samples of the films of the present disclosure were tested and compared to other types of signal composites, or the same types of signal composites having different levels of a particular ingredient. For instance, the examples demonstrate the temperature drop effect of film versus coform; cooling efficiency between coform, laminate and multilayer film; skin layer strength and swelling as affected by starch content; and the cooling efficiency of a "middle" layer.

Example 1

Figure 10:
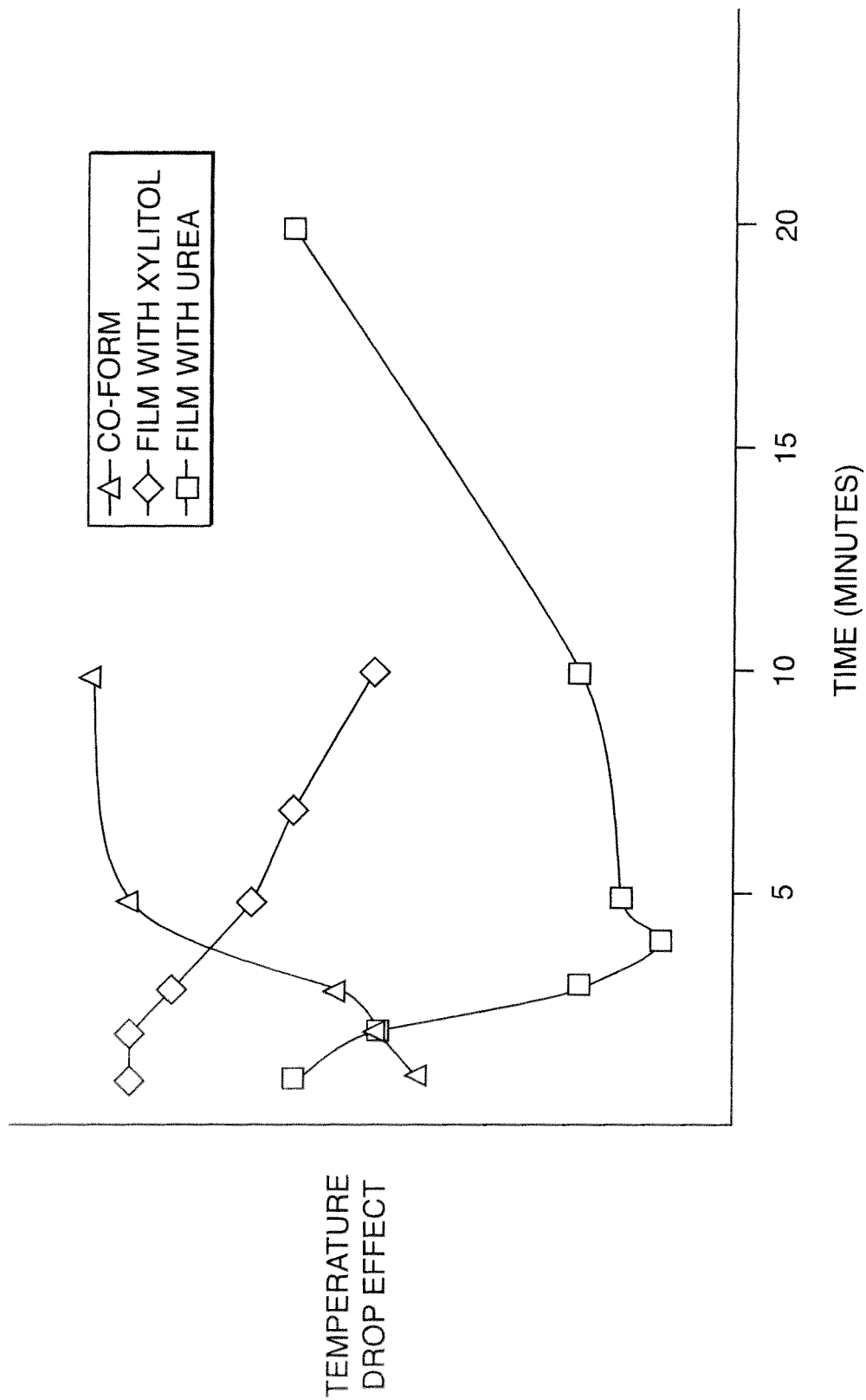
FIG. 10 is a graphical depiction of the temperature drop effect of films versus coform material.

Referring to FIG. 10, "ABA" cooling stimulant materials (e.g. the 121 structure seen in FIG. 3B) having two different middle or "B" layers are compared to a coform material with respect to a temperature drop effect over time. In one example, the B layer is made with xylitol as the cooling material. In another example the B layer is made with urea as the cooling material.

The samples made with xylitol and urea were co-extruded. The specimen size for each specimen type was 25×25 mm The total thickness of all the samples ranged from 30-35 mil (0.7-0.9 mm).

Two twin-extruders having a 27 mm screw (ZSE-HP Micro-27 twin screw with a 60/1 L/D ratio), and an ABA multi feed-block with a 10 inch die were used to the ABA multilayer cooling material. These extruders may be obtained from American Leistritz Corp, Somerville, N.J., U.S.A.

For the xylitol samples, the "A" layers were made with EVP polymer 8705 from the Exxon Mobile Chemical Company, extruded at 2.5 lb/hour; and Glucosol 800 from Chemstar Products Company, Minneapolis, Minn., U.S.A. extruded at 1.0 lb/hour. The extrusion condition for the A layers: zones 1-3 were at 100 degrees C.; zones 4-7 were at 80 degrees C., zones 8-10 were at 70 degrees C.; and zones 11-13 were at 77 degrees C. The B layer was a combination of 2.5 lb/hr of xylitol powder, EVP polymer 8705 (used as a binder) extruded at 3.5 lb/hour, and glycerin (used as a plasticizer) extruded at 0.5 lb/hour. The extrusion conditions for the B layers: zones 1-11 were at 70 degrees C. The ABA die temperature was at 77 degrees C. The middle layer was 90 percent by weight of the total ABA composite.

For the urea samples, the "A" layers were made with EVP polymer 8705 form Exxon Mobile Chemical Company, extruded at 3 lbs/hour; and Glucosol 800 extruded at 1 lb/hour. The B layer was a combination of urea extruded at 16 lbs/hour, EVA 8705 at 5 lbs/hour and glycerin (used as a plasticizer) extruded at 0.5 lbs/hour. The extrusion temperature was 100-110 degrees C. The samples had a thickness of about 30-35 mil (0.7-0.9 mm) The middle layer was 70-80 percent by weight of the total ABA composite.

The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith. The coform specimens used in the current example were made with about 10-15% polymer fibers, about 15% pulp, and about 70-75% sorbitol by weight. The web is formed on a spunbond carrier sheet.

As seen in FIG. 10, when each specimen was insulted, the temperature drop was determined per the Temperature Measurement of Sheet Materials test method, described herein. Within a ten minute period, the coform quickly returned to the ambient temperature (see the temperature drop effect from −1 to −0.2). In that same period, the film specimen made with xylitol had a temperature effect from about −0.3 to −0.9. Also in the same period, the film specimen made with urea had a temperature effect that dramatically went from −0.7 to −1.4. Unlike the other two samples, the urea specimen was coolest after about 3.5 minutes, demonstrating a −1.6 temperature drop effect. The urea multilayer cooling-film had an extended cooling period from ten to twenty minutes. The urea specimen gradually warmed as shown. In contrast, the coform temperature drop effect is much smaller and the cooling period much shorter than the urea multilayer cooling-film.

Example 2

Figure 11:
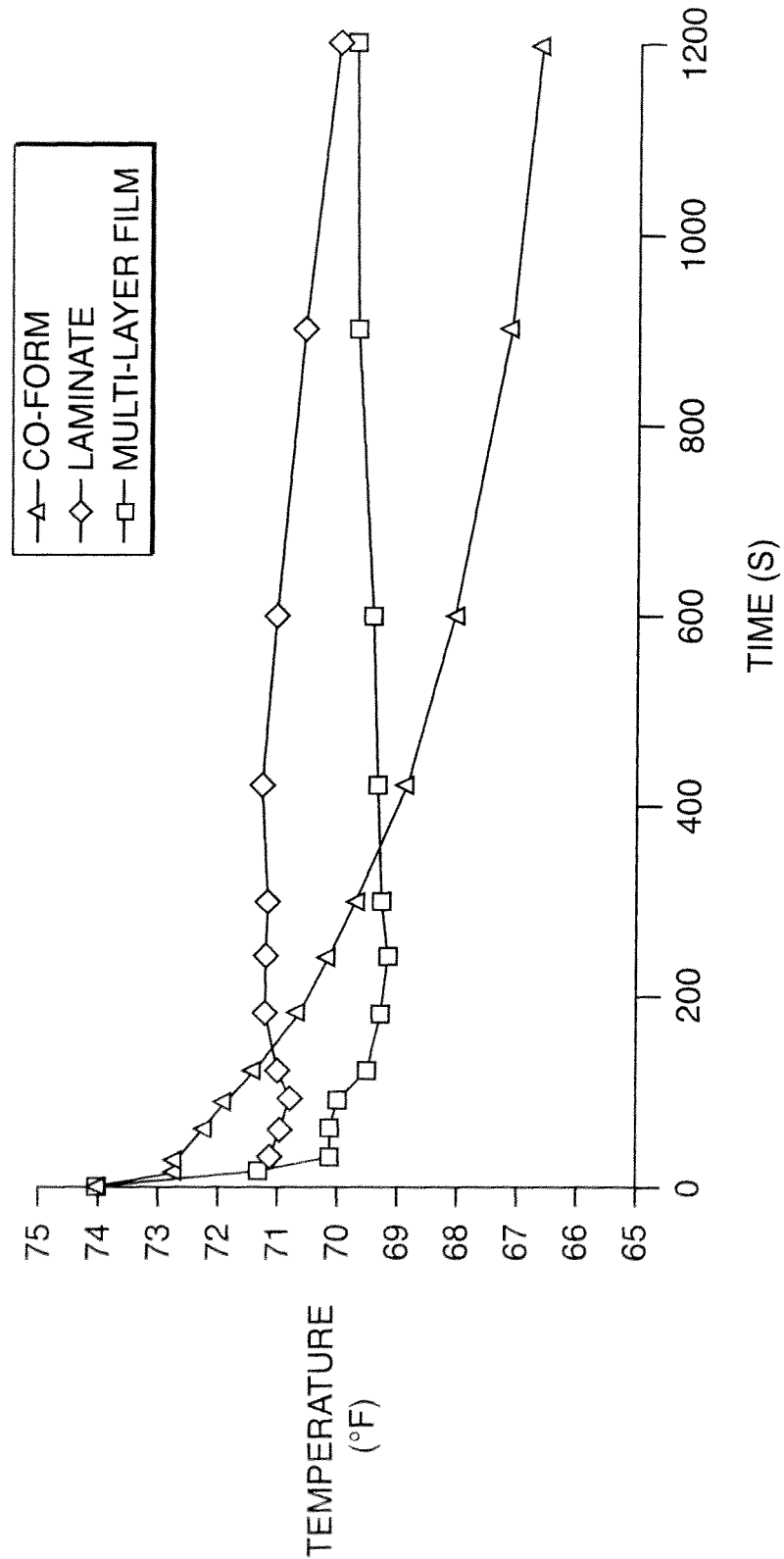
FIG. 11 is a graphical depiction of the cooling efficiency of coform, laminate and multi-layered film materials.

Referring to FIG. 11, it is seen that co-form provides almost instant cooling and returns back to room temperature. This happens in part because the cooling agent is readily soluble and absorbs heat. In addition, cooling occurs by evaporation. The cooling agent is absorbed into the absorbent core, diminishing the cooling effect. The low cooling efficiency demonstrated by the coform may be partially due to having cooling agent washed away by an insult to other parts of the absorbent article. In addition, the cooling effect from the dissolution of cooling agent can be overshadowed by the temperature of the insult.

In contrast, the film of the present disclosure provides relatively long lasting cooling in a more controllable way. As shown in FIG. 11, the cooling effect of the multilayer film lasted much longer and was more efficient because the cooling agents that remained were kept inside the cooling laminate by the skin layer.

Example 3

Figure 12:
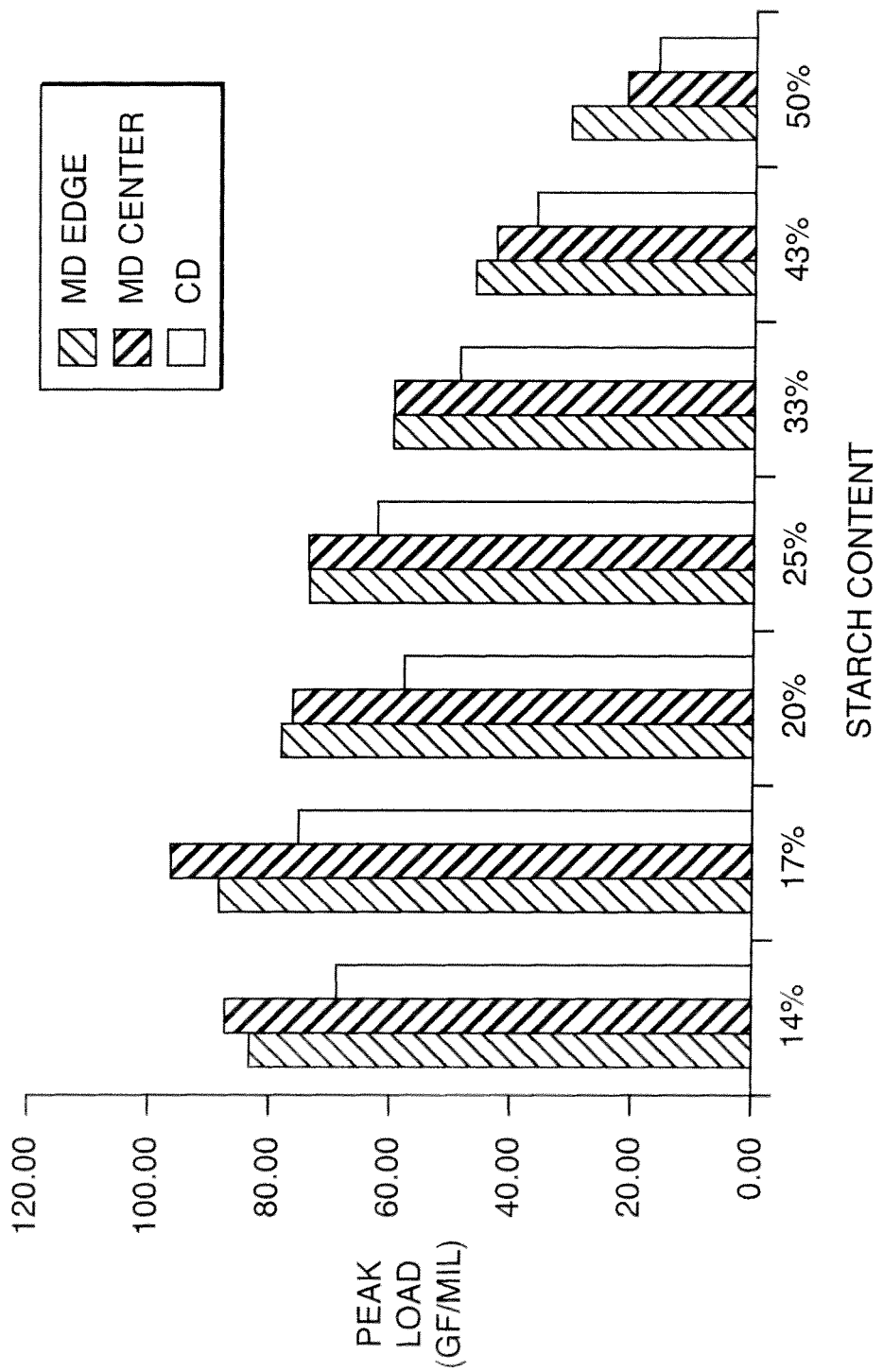
FIG. 12 is a graphical depiction of skin-layer strength comparisons of films having different starch content.

Referring to FIG. 12, two layers of ABA film (middle layer and two skin layers) are made of different components. The skin layer is made from a mixture of ethyl vinyl acetate (EVA) and a water-soluble thermal starch glucosol. The middle layer is made of the cooling agent and a polymer binder (e.g. Polyethylene glycol). It is thought that by changing the concentration of each of these components, the physical properties were also changed.

The graph of FIG. 12 shows that as the concentration of starch increases, the film weakens. As can be seen, a film with fifty percent starch has a peak load in the cross-direction (CD) of less than 20 gf/mil, which is undesirable with respect to tensile strength. The tensile strength was tested according to the ASTM Tensile Test described herein.

Example 4

Figure 13:
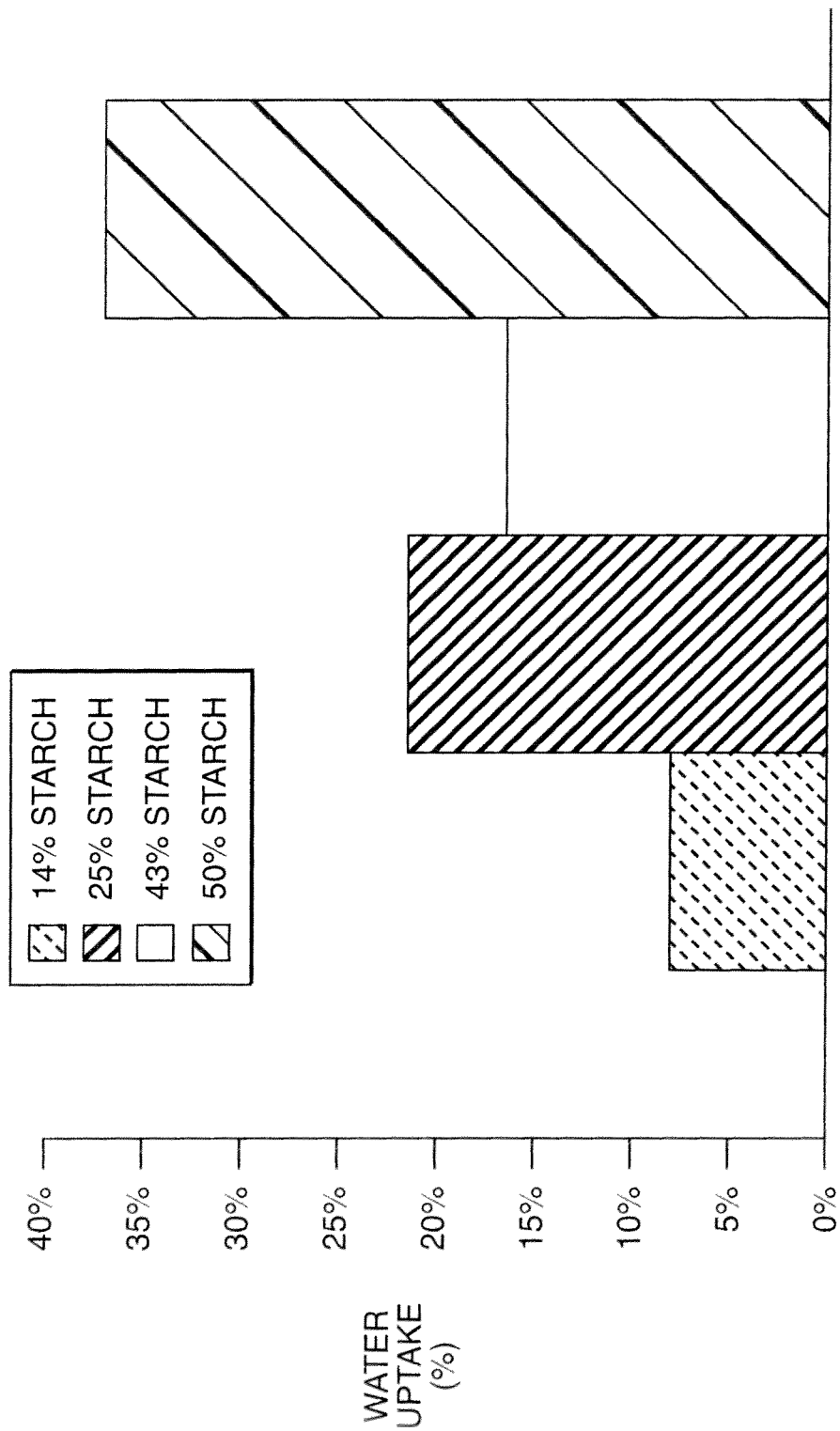
FIG. 13 is a graphical depiction of skin-layer water uptake as it correlates to starch content.

Referring to FIG. 13, shown is the water uptake for the various film samples. Because of the variability of the film samples, the films with starch concentrations of 14%, 25%, 43% and 50% were tested according to the Water Uptake test described herein Films containing 50 percent starch by weight had significantly greater water uptake than the other specimens.

Example 5

Figure 14:
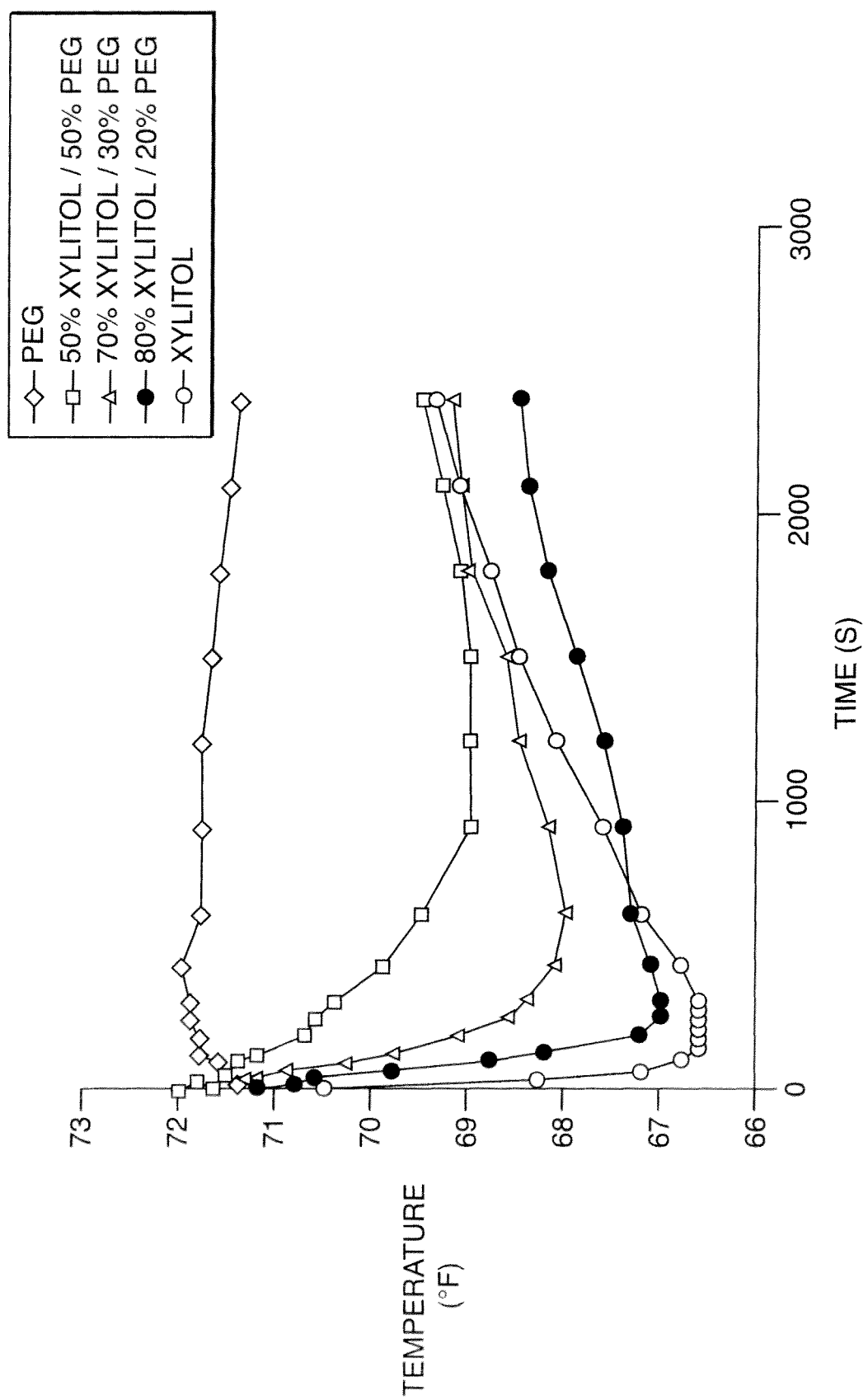
FIG. 14 is a graphical depiction of cooling performance between four film aspects.

Referring to FIG. 14, it is shown that as the concentration of PEG increases, the cooling efficiency of the middle layer become slower, and that the cooling efficiency that occurs is directly proportional to amount of cooling agent in the film. Thus, the rate of cooling can be controlled through the percentage amount of cooling agent versus PEG in the middle layer. As can be seen, the cooling efficiency of the middle layer with 80% xylitol/20% PEG is comparable to that of 100% xylitol pure component.

Test Methods

Unless otherwise noted, all tests are performed at a temp of 23±2° C. and a relative humidity of 50±5%.

Thickness Test

Figure 16:
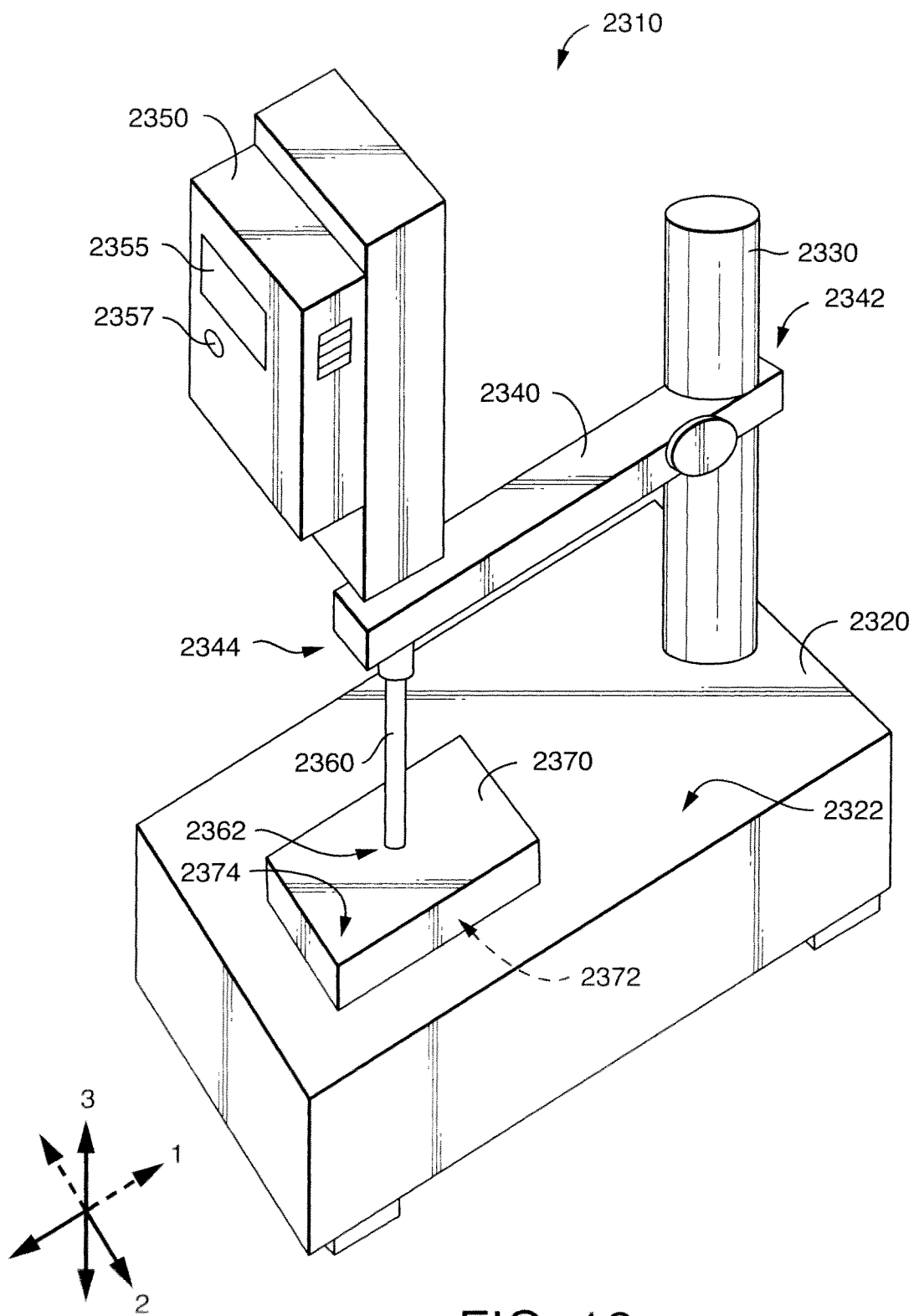
FIG. 16 is a perspective view of a thickness tester utilized in the Thickness Test.

The thickness value of a selected portion or section of an article is determined using a thickness tester such as seen in FIG. 16. The thickness tester 2310 includes a granite base 2320 having a clamp shaft 2330 where the top surface 2322 of the granite base 2320 is flat and smooth. A suitable granite base is a Starret Granite Base, model 653G (available from The L.S. Starrett Company, having a place of business located in Athol, Mass., U.S.A.) or equivalent. A clamp arm 2340 is secured to the clamp shaft 2330 at one end 2342 of the clamp arm 2340, and a digital indicator 2350 is secured to the clamp arm 2340 at the opposing end 2344. A suitable indicator is a Mitutoyo ID-H Series 543 Digimatic Indicator (available from Mitutoyo America Corp., having a place of business located in Aurora, Ill., U.S.A.) or equivalent. Extending downward from the indicator 2350 is a vertically-movable plunger 2360.

To perform the procedure, a block 2370 having a length of 50 mm and a width of 44 mm is placed onto the granite base 2320. The block 2370 is constructed of acrylic and is flat and smooth on at least the bottom surface 2372. The thickness and weight of the block 2370 is configured such that the thickness tester 2310 provides a pressure to the sample of 0.69 kPa (0.1 psi). Next, the thickness tester 2310 is gently lowered such that the bottom surface 2362 of the plunger 2360 is in direct contact with the top surface 2374 of the block 2370 at the longitudinal 1 and transverse 2 center of the block 2370, and the plunger length is shortened by about 50%. The digital indicator 2350 is then tared (or zeroed) by pressing the "zero" button 2357. The digital display 2355 of the digital indicator 2350 should display "0.00 mm" or equivalent. The thickness tester 2310 is then raised and the block 2370 is removed. The test sample is then placed onto the top surface 2322 of the granite base 2320 and the block 2370 is gently placed on top of the test sample such that the block 2370 is substantially centered longitudinally 1 and transversely 2 on the sample. The thickness tester 2310 is then gently lowered again onto the block 2370 such that the bottom surface 2362 of the plunger 2360 is in direct contact with the top surface 2374 of the block 2370 at the longitudinal 1 and transverse 2 center of the block 2370, and the plunger length is shortened by about 50%, to provide a pressure of 0.69 kPa (0.1 psi). After 3 seconds, the measurement from the digital display 2355 is recorded to the nearest 0.01 mm.

Temperature Measurement of Sheet Materials (Film, Coform, Laminate)

A method to compare the cooling efficiencies of different sheet materials is as follows. A 3 inch by 3 inch (7.62 cm by 7.62 cm) section of signal composite sheet and 30 ml of de-ionized water are placed into an insulated beaker. A temperature probe is placed on the surface of the composite sheet to measure temperature change.

Tensile Strength Test

For the tensile strength test, ASTM D638-08 is used. Samples from each film are taken from the MD (machine direction) at the edge and center as well as the CD (cross direction).

Water Uptake Test

A 1 inch by 1 inch (2.54 cm by 2.54 cm) sample of the signal composite is placed in a beaker of 50 ml of 0.9% saline for one hour. The mass was measured before and after test to calculate the percentage of water uptake. A higher concentration of starch will increase the water uptake. The starch increases the hydrophilicity to allow more water absorption.

It will be appreciated that details of the foregoing examples, given for purposes of illustration, are not to be construed as limiting the scope of this disclosure. Although only a few exemplary aspects of this disclosure have been described in detail above, those skilled in the art will readily appreciate that many modifications are possible in the examples without materially departing from the novel teachings and advantages of this disclosure. For example, features described in relation to one example may be incorporated into any other example of the disclosure. While a training pant has been described above for exemplary purposes, it is understood that the signal composite of the present disclosure can be suitable for other personal care absorbent articles such as feminine care pads, incontinence garments and the like.

Accordingly, all such modifications are intended to be included within the scope of this disclosure, which is defined in the following claims and all equivalents thereto. Further, it is recognized that many aspects of the disclosure that may be conceived that do not achieve all of the advantages of some aspects, particularly of the desirable aspects, yet the absence of a particular advantage or technical effect shall not be construed to necessarily mean that such an aspect is outside the scope of the present disclosure. As various changes could be made in the above constructions without departing from the scope of the disclosure, it is intended that all matter contained in the above description shall be interpreted as illustrative and not in a limiting sense.

The invention claimed is:

1. A signal device comprising;
    a signal composite that comprises a coextruded film having two layers, wherein the two layers are a first polymer skin layer comprising a water-soluble polymer and/or a water swellable polymer, and a stimulation layer comprising a first cooling agent and a polymer binder;
    wherein the stimulation layer comprises 50 to 98 percent by weight of the signal composite.

2. The signal device of claim 1 wherein the water-soluble and/or water-swellable polymer is selected from the group consisting of modified thermal starch, polyvinyl alcohol, acrylic polymer, polyethylene oxide, polyethylene glycol, polyacrylamide, polyester, ethylene vinyl acetate copolymer and a combination thereof.

3. The signal device of claim 1 wherein the polymer binder is water-soluble and/or water-swellable.

4. The signal device of claim 1 wherein the first cooling agent is selected from the group consisting of xylitol, sorbitol, urea and a combination thereof.

5. The signal device of claim 1 further comprising a second polymer skin layer attached to a surface of the stimulation layer opposite the first polymer skin layer, such that the stimulation layer is disposed between the first and second polymer skin layers.

6. The signal device of claim 5 further comprising a coextruded third layer attached to the second polymer skin layer.

7. The signal device of claim 6 wherein the coextruded third layer comprises a second stimulation layer, and wherein the second stimulation layer comprises a second cooling agent that is different in composition from the first cooling agent.

8. The signal device of claim 5 wherein the second polymer skin layer comprises a water-soluble polymer and/or water swellable polymer.

9. The signal device of claim 1 wherein the first polymer skin layer is insoluble.

10. The signal device of claim 9 wherein the first polymer skin layer having perforations therein allows liquid to reach the stimulation layer.

11. The signal device of claim 1 wherein the first polymer skin layer is 2 to 10 percent of the total weight of the signal composite.

12. The signal device of claim 1 further comprising a web bonded to the signal composite.

13. The signal device of claim 12 further comprising an adhesive for binding the web to the signal composite.

14. A signal composite laminate comprising;
a first coextruded film comprising two layers, wherein the two layers of the first coextruded film are a first outer skin layer comprising a water-soluble and/or water-swellable polymer, and a first stimulation layer comprising a cooling agent and a first polymer binder; and
a second coextruded film having two layers, wherein the two layers of the second coextruded film are a second outer skin layer comprising a water-soluble polymer and a second stimulation layer comprising a second polymer binder;
wherein the first coextruded film is bonded to the second coextruded film; and
wherein the first stimulation layer comprises 50 to 98 percent by weight of the first coextruded film.

* * * * *